United States Patent
Pentafragas

(10) Patent No.: US 7,318,435 B2
(45) Date of Patent: Jan. 15, 2008

(54) DRY POWDER INHALER

(76) Inventor: Dimitrios Pentafragas, 17 Elaionon Street, GR-190 09, Pikermi, Attika (GR)

( * ) Notice: Subject to any disclaimer, the term of this patent is extended or adjusted under 35 U.S.C. 154(b) by 36 days.

(21) Appl. No.: 10/506,940

(22) PCT Filed: Sep. 25, 2002

(86) PCT No.: PCT/GR02/00050

§ 371 (c)(1),
(2), (4) Date: Sep. 8, 2004

(87) PCT Pub. No.: WO03/082389

PCT Pub. Date: Oct. 9, 2003

(65) Prior Publication Data

US 2005/0252511 A1    Nov. 17, 2005

(30) Foreign Application Priority Data

Mar. 29, 2002  (GR) .............................. 020100159

(51) Int. Cl.
*A61M 15/00* (2006.01)

(52) U.S. Cl. .............................. 128/203.21; 128/203.15

(58) Field of Classification Search .......... 128/200.23, 128/203.15, 203.19, 203.21; 206/528, 532, 206/531, 536, 358, 540, 828; 221/25, 31; 222/81–83

See application file for complete search history.

(56) References Cited

U.S. PATENT DOCUMENTS

| | | | |
|---|---|---|---|
| 5,035,237 A * | 7/1991 | Newell et al. ......... | 128/203.15 |
| 5,590,645 A | 1/1997 | Davies et al. | |
| 5,740,794 A * | 4/1998 | Smith et al. ........... | 128/203.15 |
| 6,029,663 A * | 2/2000 | Eisele et al. ........... | 128/203.21 |
| 6,032,666 A | 3/2000 | Davies et al. | |
| 6,257,232 B1 * | 7/2001 | Andersson et al. .... | 128/203.15 |
| 6,367,473 B1 * | 4/2002 | Kafer ..................... | 128/203.21 |
| 6,604,522 B2 * | 8/2003 | Arvidsson et al. ..... | 128/203.15 |
| 6,722,363 B1 * | 4/2004 | Von Schuckmann ... | 128/203.15 |
| 6,907,880 B1 * | 6/2005 | Heckenmuller et al. ..................... | 128/203.15 |
| 6,941,947 B2 * | 9/2005 | Young et al. .......... | 128/203.21 |
| 7,171,965 B2 * | 2/2007 | Young et al. .......... | 128/203.15 |

FOREIGN PATENT DOCUMENTS

| | | |
|---|---|---|
| EP | 0 129 985 | 1/1985 |
| EP | 0129985 | 1/1985 |
| EP | 0 467 172 | 1/1992 |
| EP | 0 469 814 | 2/1992 |
| HU | 220 182 | 11/2001 |
| HU | 223 431 | 7/2004 |
| WO | 92/04069 | 3/1992 |
| WO | 92/10230 | 6/1992 |

(Continued)

*Primary Examiner*—Teena Mitchell
(74) *Attorney, Agent, or Firm*—Ladas and Parry, LLP

(57) ABSTRACT

An inhalation device for the uptake of medicaments that are in the form of dry powder contained in the blisters of specially designed single dose blister strips. The device is comprised of a mouthpiece (A), a strip support surface area (B). and one or more storage areas (C). Furthermore, the single dose blister strip is described. It is comprised of two sheets (17, 20) that are fixed in such a manner so that when they get separated the powder becomes available for inhalation.

12 Claims, 7 Drawing Sheets

6A    6B    6C

FOREIGN PATENT DOCUMENTS

| | | |
|---|---|---|
| WO | 93/17728 | 9/1993 |
| WO | 97/02061 | 1/1997 |
| WO | 98/34663 | 8/1998 |
| WO | 9834663 | 8/1998 |
| WO | 00/64779 | 11/2000 |
| WO | 0064779 | 11/2000 |
| WO | 2004/012802 | 2/2004 |

* cited by examiner

DRY POWDER INHALER

BACKGROUND OF THE INVENTION

The present invention refers to an inhaler for the uptake of medicaments in the form of dry powder and to specialty designed single dose blister strips that are used with the said inhaler.

FIELD OF THE INVENTION

The inhaling devices currently used can be separated into two categories:

1. Those where the pharmaceutical powder is stored in a container out of which a measured amount of powder can be released via specific mechanisms. EP0069715 for example, describes a device in which the powder is metered in given dosages through apertures located in a rotatable disc, these apertures being introduced into an airduct or channel through which air is inhaled, by rotating the disc.

DESCRIPTION OF PRIOR ART

2. Those where measured amounts of pharmaceutical powder can be stored separately in special containers. GB2242134 for example, describes a device which uses a flexible strip defining a plurality of pockets each of which contains a dose of medicament which can be inhaled. The device contains a chamber in which the strip is housed, an opening station which contains means for peeling the two sheets or the strip apart and an outlet through which the user can inhale the medicament.

The major disadvantages of these and other similar devices are that a. the user cannot visually verify whether he has received the entire dose of the medicament, and b. they function through complicated internal mechanisms.

SUMMARY OF THE INVENTION

The advantage of the present invention is that the user can visually check the presence of the medicament in the blister of the strip prior to inhalation and verify after the inhalation that he has received the entire dose of the medicament. Additionally, the device is simple to manufacture and easy to operate.

The device of the present invention is comprised of three parts: the mouthpiece, through which the powder is inhaled, the blister strip support surface and the strip storage compartment(s), which house(s) a large number of blister strips. The three parts are connected to each other and can be independently opened. The support surface contains an attachment point, where the blister strip is attached with the help of an attachment formation; a cavity, which accommodates the blister of the strip; and strip guides, which secure the proper and firm placement of the strip on the surface. The single dose blister strip is comprised of two sheets that can be pealed away from each other. The base sheet has a blister which contains the powder, and an attachment formation which fits to the attachment point of the support surface. The cover sheet seals the base sheet only in the area around the blister. The principle of use is that the user securely attaches the blister strip on the attachment surface, pulls away the cover sheet of the blister by exercising a slight force, checks the content of the blister, inhales the medicament, and finally verifies that he has received the entire dose.

BRIEF DESCRIPTION OF THE DRAWINGS

FIG. 1 shows different views of an example of an inhaler.
FIG. 2 shows the mouthpiece of the device along with its component parts.
FIG. 3 shows the part of the device that contains the area on which the blisters are placed.
FIG. 4 shows the blister storage compartment.
FIG. 5 shows a single dose blister strip and the way it is put together.
FIG. 6 shows the process that reveals the powder in the blister.
FIG. 7 shows the flow of air and powder during the inhalation process.
FIGS. 8 and 9 are further examples of inhalers based on the principle of the present invention.

DETAILED DESCRIPTION OF THE INVENTION

Figure 1:
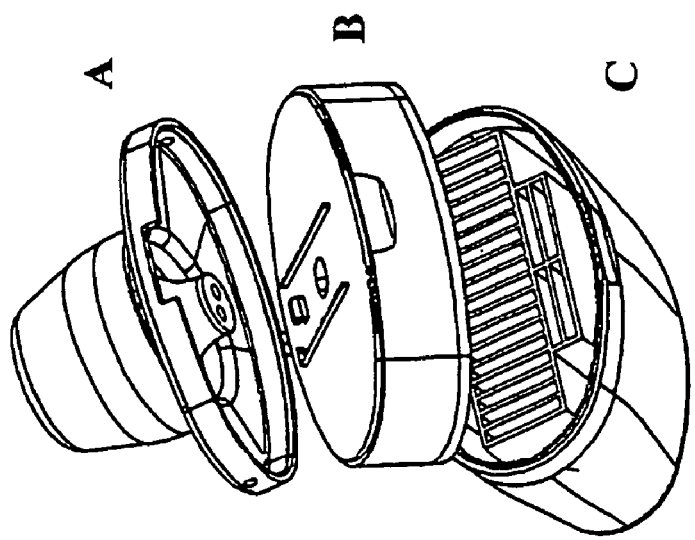
FIGS. 1-9 depict examples of the invention.
Figure 1:
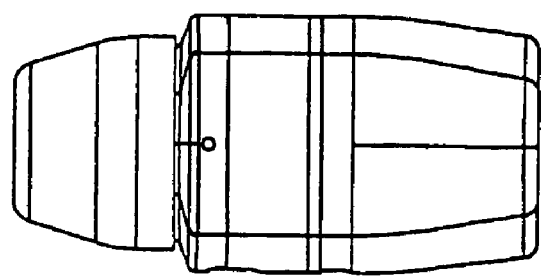
Figure 1:
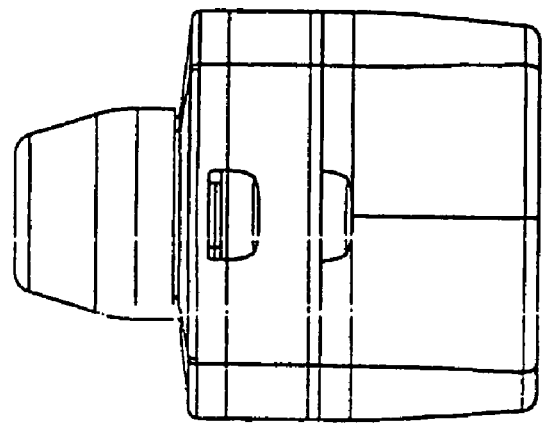

The inhaler (FIG. 1) includes 3 basic parts, the mouthpiece A with its cover, part B with the surface on which the blister strip is placed, and the blister strip storage part C. The parts are connected to each other and can be opened independently.

Figure 2:
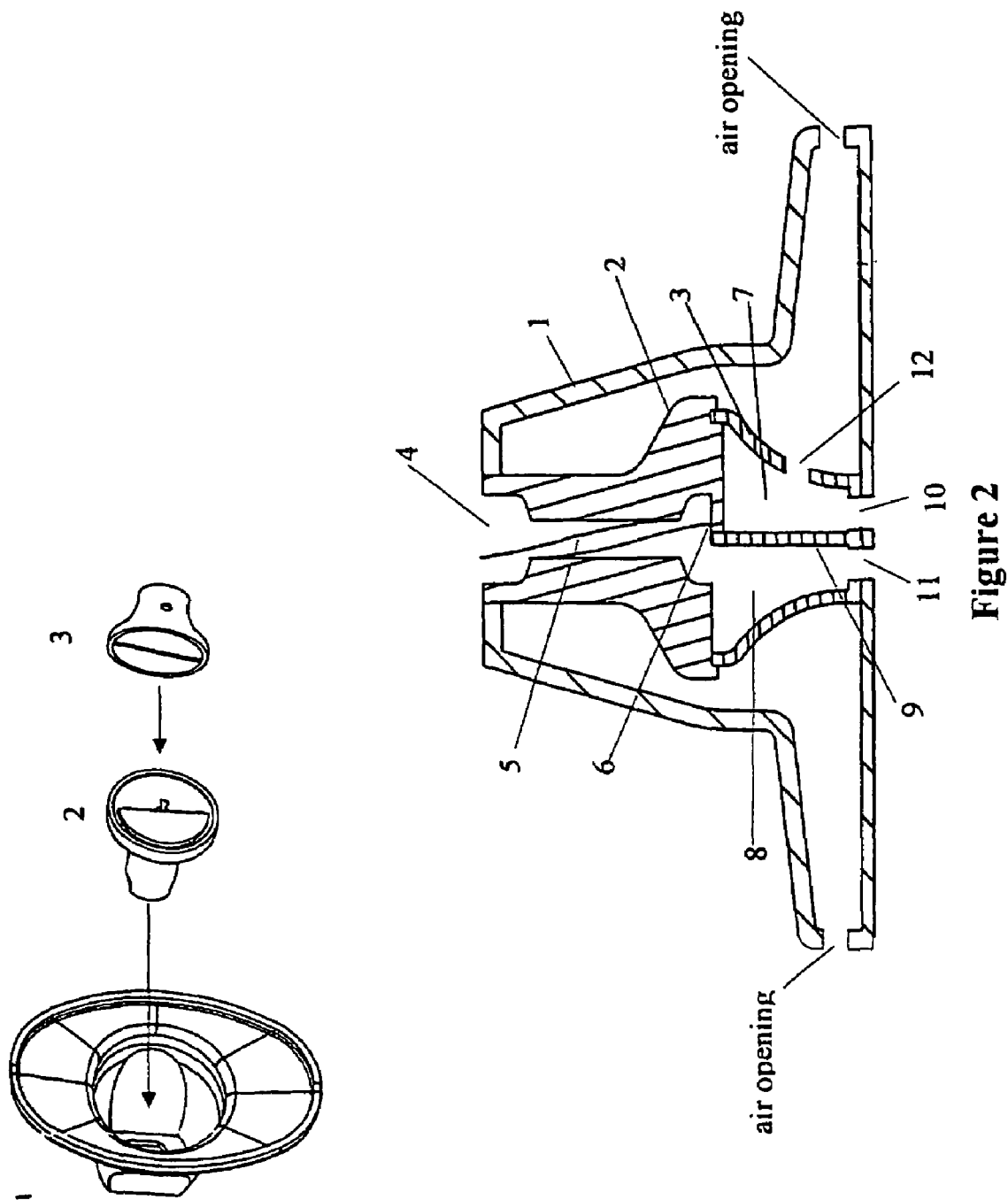

The mouthpiece (FIG. 2) is comprised of parts 1, 2 and 3. Part 1 locks in part 2 and part 2 locks in part 3.

Part 1 is the external part of the mouthpiece, and may have air openings at its base.

Part 2 is a cylinder with a wider base. The top of the cylinder has an opening 4, which serves as the exit of the powder from the device. Inside the cylinder there is formation 5, which may be of helical or other shape, through which the inhaled powder containing air exits the device. The end of formation 5 at the base of part 2 is blocked in half with surface 6.

Part 3 is also a cylinder, which has a wider top. The interior of part 3 is divided into in chambers 7 and 8, by an upright flat divider surface 9. The base of part 3 touches the blister. It has two holes, 10 and 11, one on each side of divider 9. Hole 11 may contain a sieve, in order to black the passage of larger particles. Chamber 7 contains hole 10, and is blocked at its top with surface 6. Furthermore, chamber 7 contains hole 12, which serves as the air entrance.

Figure 3:
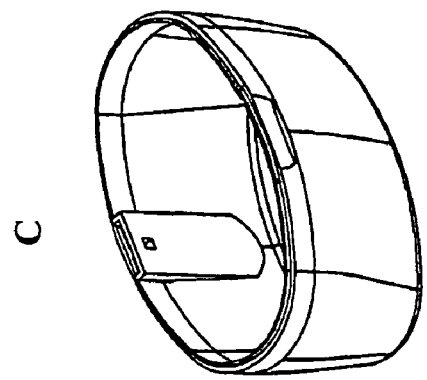
Figure 3:
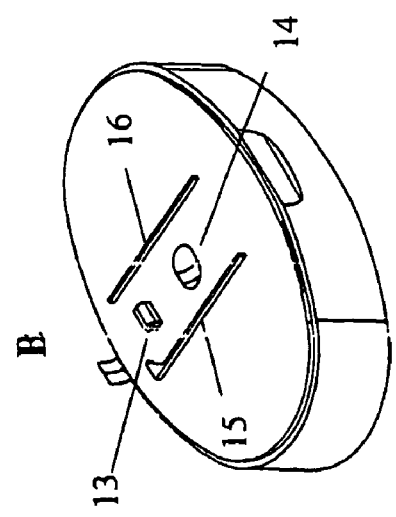

The single dose blister strip is placed on the attachment surface of part B (FIG. 3). This surface has a protrusion 13 that serves as the attachment point, a cavity 14 which receives the blister of the strip, and a system of strip guides, 15 and 16 in the specific example. The protrusion, the cavity and the guides enable the correct alignment of the strip on the surface of part B and secure its firm placement during the use of the device. The lower portion of part B can be used as a storage compartment for the blister strips.

Figure 4:
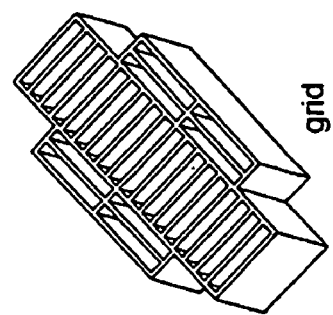

The strip storage part C (FIG. 4) can be of various shapes, and may contain a grid, depending on the number of strips it accommodates, e.g. 30 or 60.

Figure 5:
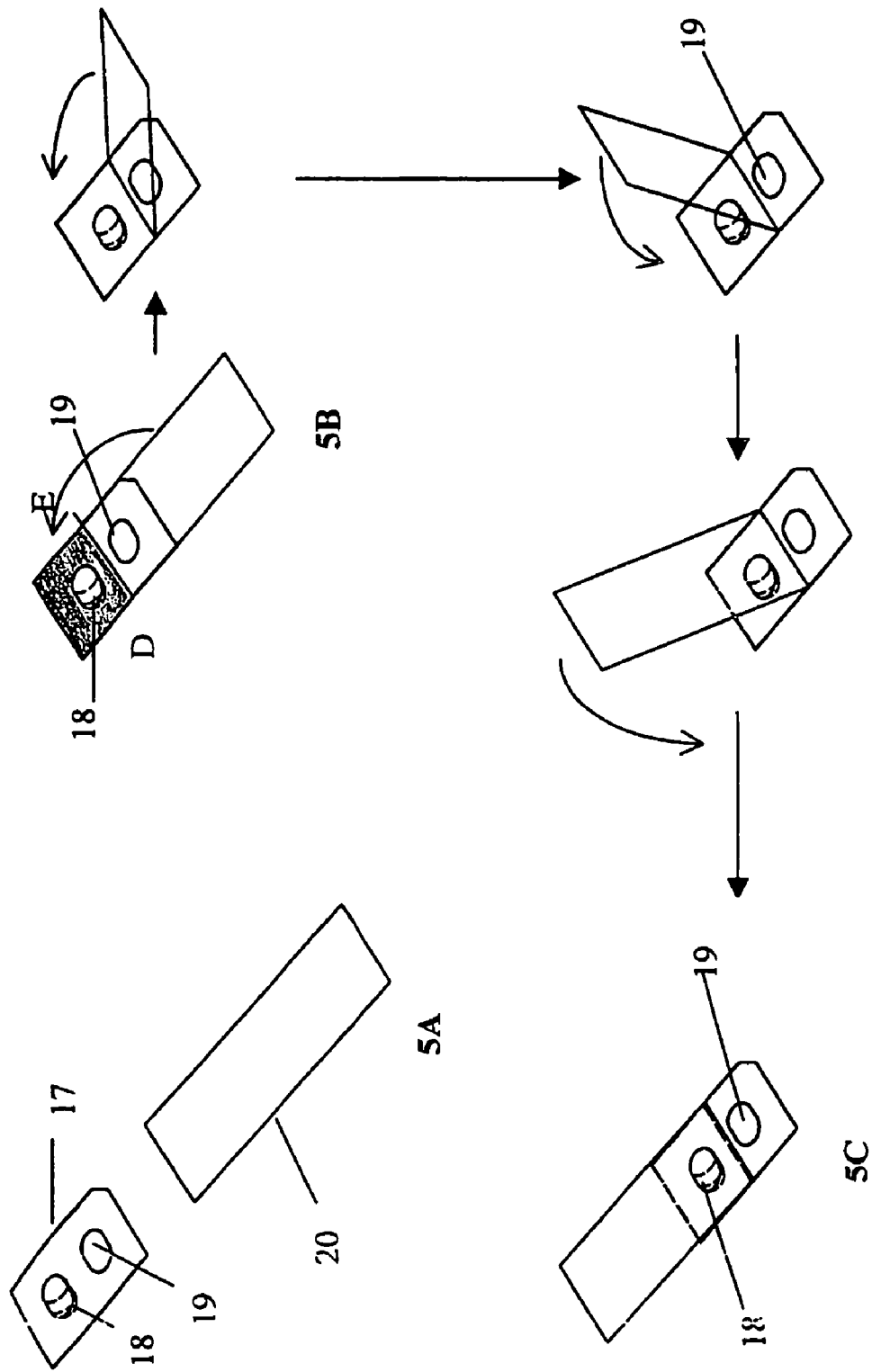

The blister strip (FIG. 5) consists of two sheets (FIG. 5A) made of suitable material e.g. PVC, aluminium, polyamide, paper, polyester, vinyl gum. One of the two sheets is the base sheet 17, which has the blister 18 that contains the powder, and the attachment hole 19. The other is the cover sheet 20 that is fixed to the base sheet, e.g. by heat adhesion, and air-tightly seals only the area around blister 18, as shown in the drawing (FIG. 5B, darkened area). Sheet 20 is then folded by a 180-degree rotation around axis DE, revealing hole 19 and covering the flat surface of blister 18 (FIG. 5C).

Figure 6:
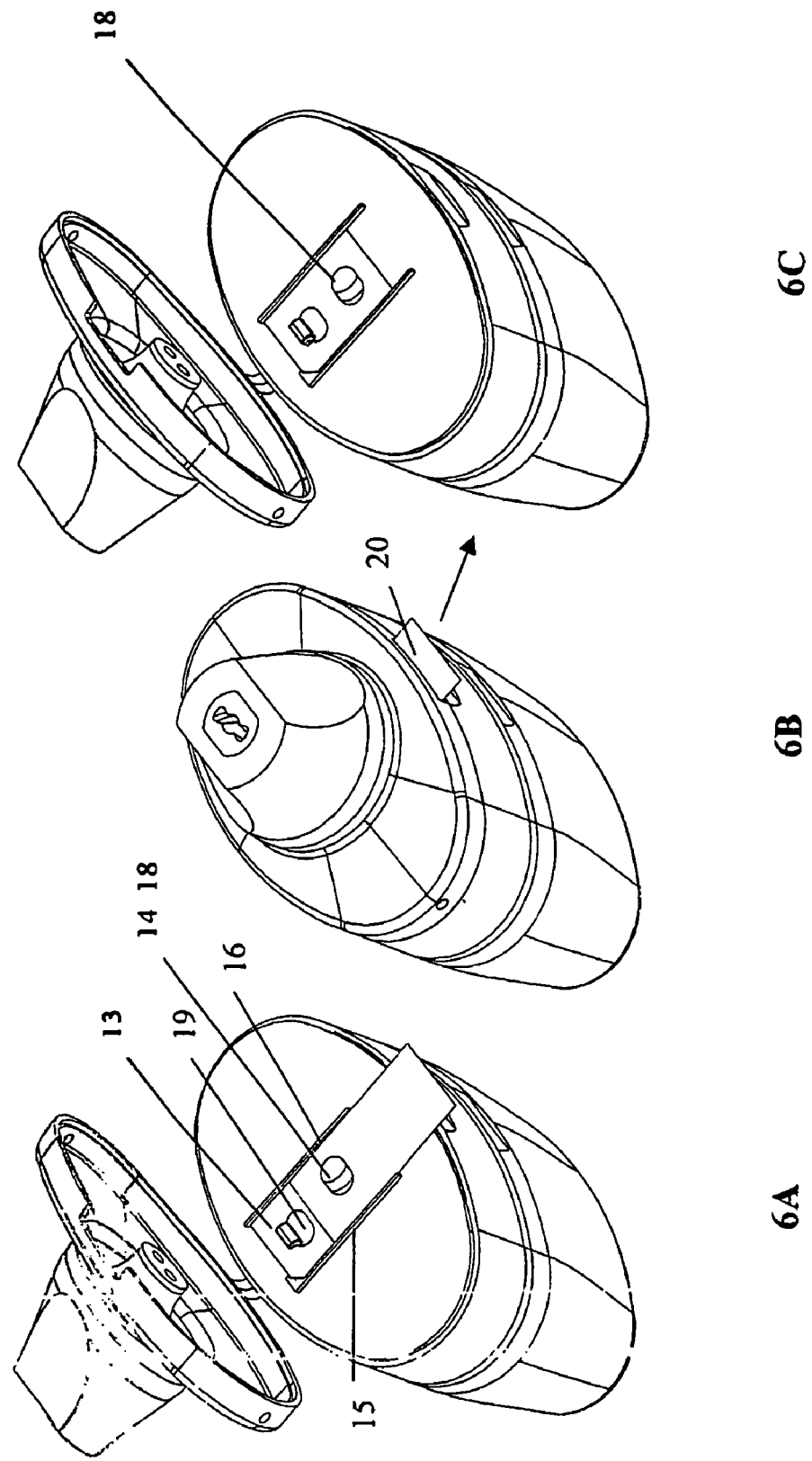

The process by which the blister-contained powder is exposed takes place in two stages (FIG. 6).

During the first stage FIG. 6A) and while the mouthpiece is open, the user secures the strip on the support surface of part B by placing hole 19 around protrusion 13. Blister 18 is then placed in cavity 14 with the assistance of guides 15 and 16. During the second stage (FIG. 6B), the user closes the mouthpiece and pulls cover sheet 20 towards the direction of the arrow until it is completely detached.

At this point and after lifting the mouthpiece, the user can verify that the powder contained in blister 18 has been revealed and is available for inhalation (FIG. 6C). The user then just closes the mouthpiece and inhales. Finally, by opening again the mouthpiece, he can visually check whether he has inhaled the medicament.

Figure 7:
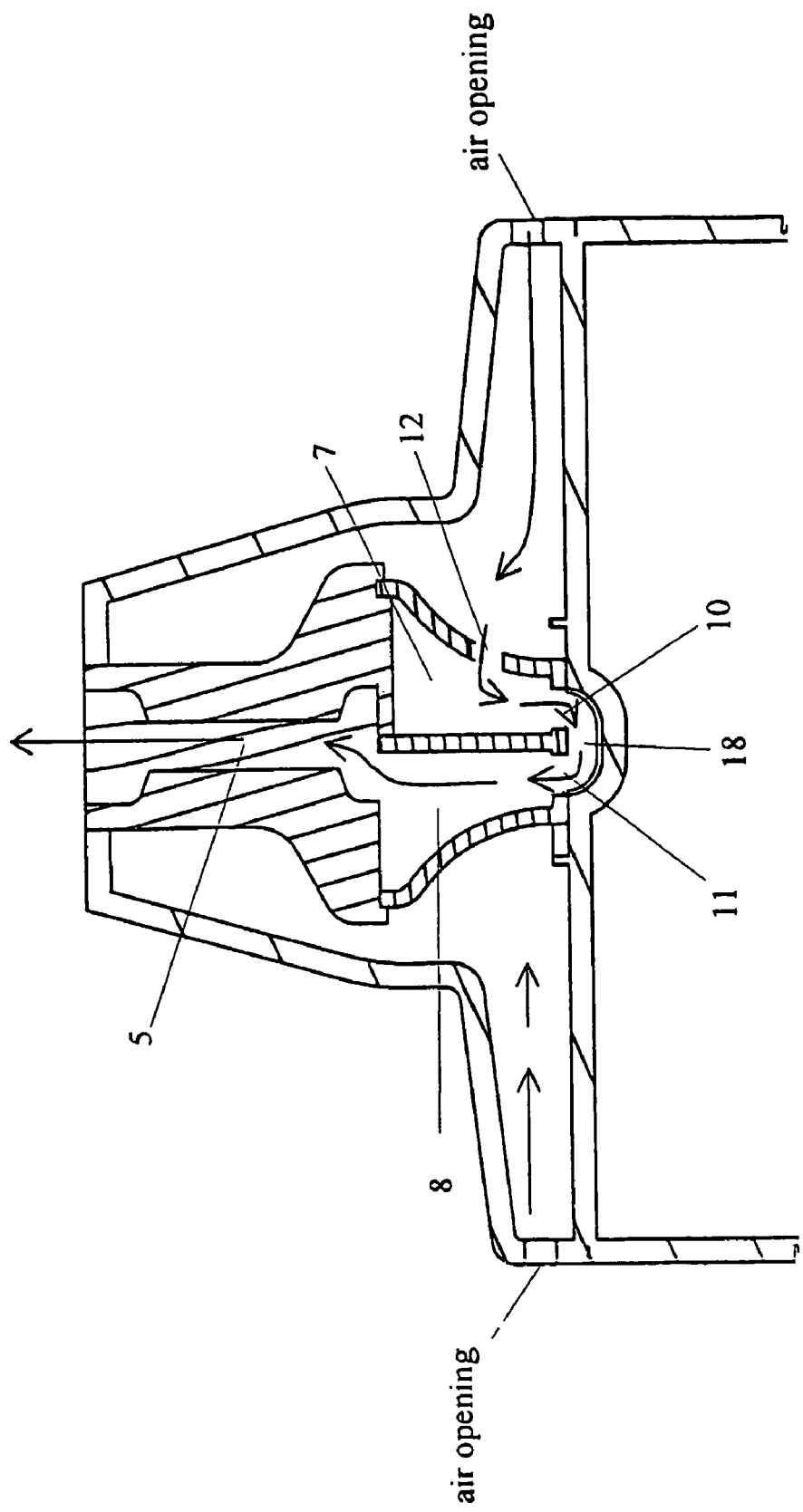

During the process of inhalation (FIG. 7) the air that is breathed-in enters the mouthpiece via the air openings, and then enters chamber 7 through hole 12. From there on and passing through hole 10, the air carries along the powder which is located in blister 18 and passing through hole 11 brings it to chamber 8. From there and through formation 5, the powder exits the device.

Figure 8:
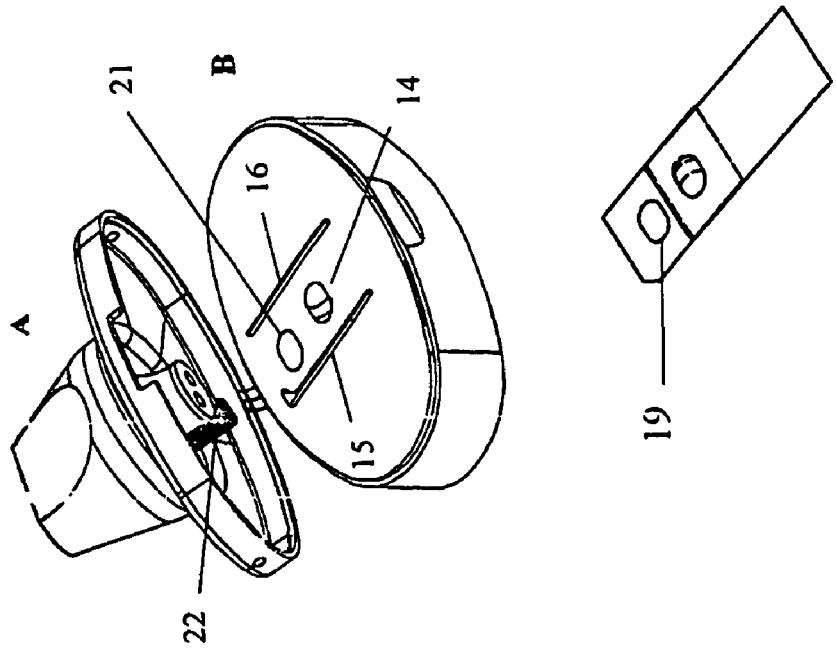

Another example of the invention is shown in FIG. 8. The attachment point for the blister strip on surface B is cavity 21. The mouthpiece A contains projection 22 which, when said mouthpiece is closed, enters cavity 21 and in this way secures the blister. In this case, the blister is placed on surface B with hole 19 above cavity 21. Alternatively, blister strip hole 19 could be replaced by a cavity.

Figure 9:
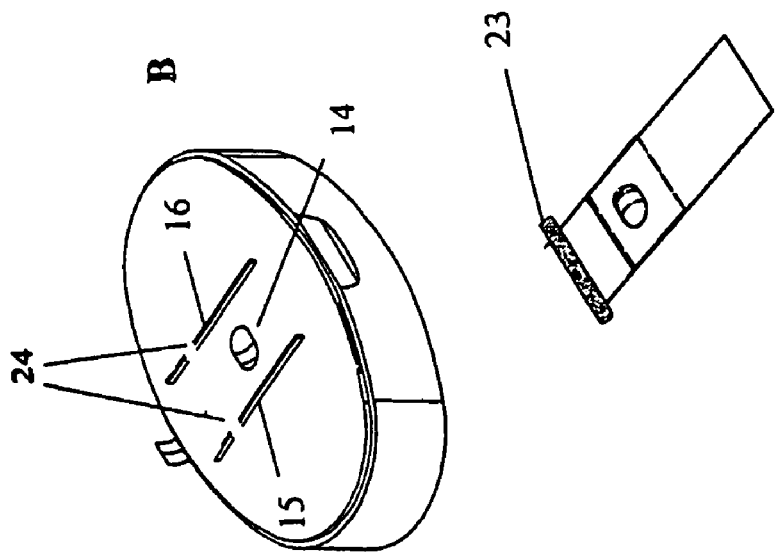

FIG. 9 shows another embodiment of the invention. In this case, the attaching component of the blister strip is formation 23 that is placed in the openings 24 of guides 15 and 16 of surface B.

It is obvious that there may be variations relating to the shape and the positions of the attachment point, the cavity and the guides on surface B, which can achieve appropriate and secure attachment of the blister. All these different embodiments are also included in the scope of the present invention.

A further embodiment of the inhaler would include its use through the nose. This could be achieved by substituting the mouthpiece with the appropriate attachment.

The invention claimed is:

1. A device for the inhalation of medicaments in the form of dry powder stored in single dose blister strips comprising a base sheet and a cover sheets, which device includes
   a mouthpiece through which the powder is inhaled,
   a part with a blister strip support surface wherein said surface includes
   a cavity which accommodates the blister and
   a strip storage compartment
wherein the blister strip support surface further includes an attachment point and strip guides and wherein the mouthpiece is openably connected to said part comprising the blister strip support surface; and wherein the cavity and guides are located such that exposure of the powder may be effected by pulling away the cover sheet from the base sheet in a direction which lies in a plane perpendicular to the attachment point and directly away from said attachment point.

2. A device according to claim 1, wherein the mouthpiece is comprised of three parts whereby the first part locks in the second part and the second part locks in the third part, said first part being an external part of the mouthpiece, said second part being a cylinder with a wider base, whose top serves as an exit of the powder from the device and whose base locks to the top of the third part, said third part being a cylinder with a wider top which contains a side hole as air entrance and whose base contains two holes which touch the blister when a blister strip is inserted into the device.

3. An inhalation device according to claim 2, wherein the second part comprises a base portion and contains within it a helical formation whose end at the base of said part is blocked in half by a surface; wherein the third part is divided in two chambers by an upright flat surface and wherein the top of the chamber which contains the air entrance hole is blocked by a surface.

4. A device according to claim 3, wherein the single dose blister strip is comprised of a base sheet which defines a blister that contains the powder and an attachment formation and a cover sheet which is air-tightly sealed to the base sheet in the area around the blister (18) and can be detached from the base sheet.

5. An inhalation device according to claim 2, wherein the attachment point is adapted to cooperate with an attachment formation on said blister strip which is in the form of a hole.

6. A device according to claim 2 wherein the mouthpiece contains a projection.

7. A device according to claim 2, wherein the attachment point is a protrusion.

8. A device according to claim 2, wherein the single dose blister strip is comprised of a base sheet which defines a blister that contains the powder and an attachment formation and a cover sheet which is air-tightly sealed to the base sheet in the area around the blister and can be detached from the base sheet.

9. A device according to claim 1, wherein the mouthpiece contains a projection.

10. A device according to claim 9, wherein the single dose blister strip is comprised of a base sheet which defines a blister that contains the powder and an attachment formation and a cover sheet which is air-tightly sealed to the base sheet in the area around the blister and can be detached from the base sheet.

11. A device according to claim 1, wherein the attachment point is a protrusion.

12. An inhalation device according to claim 1, wherein the single dose blister strip is comprised of a base sheet which defines a blister that contains the powder and an attachment formation and a cover sheet which is air-tightly sealed to the base sheet in the area around the blister and can be detached from the base sheet.

* * * * *